US007968839B2

(12) United States Patent
Merenda et al.

(10) Patent No.: US 7,968,839 B2
(45) Date of Patent: Jun. 28, 2011

(54) MINIATURIZED OPTICAL TWEEZERS BASED ON HIGH-NA MICRO-MIRRORS

(75) Inventors: Fabrice Merenda, Lausanne (CH); Johann Rohner, Le Lieu (CH); René Salathe, Ecubiens (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 294 days.

(21) Appl. No.: 12/375,058

(22) PCT Filed: Jul. 25, 2007

(86) PCT No.: PCT/IB2007/052955

§ 371 (c)(1), (2), (4) Date: Apr. 14, 2009

(87) PCT Pub. No.: WO2008/012767

PCT Pub. Date: Jan. 31, 2008

(65) Prior Publication Data

US 2010/0019136 A1 Jan. 28, 2010

(51) Int. Cl.
*H01S 3/00* (2006.01)
*C12M 3/00* (2006.01)

(52) U.S. Cl. .................. 250/251; 435/288.7; 250/492.1

(58) Field of Classification Search .................... 435/71, 435/72, 287.2, 288.7; 250/251, 461.2, 492.1
See application file for complete search history.

(56) References Cited

U.S. PATENT DOCUMENTS

| | | | | |
|---|---|---|---|---|
| 5,689,109 | A | 11/1997 | Schütze | |
| 7,628,865 | B2 * | 12/2009 | Singh | 134/1 |
| 7,759,635 | B2 * | 7/2010 | Boer et al. | 250/251 |
| 2003/0032204 | A1 | 2/2003 | Walt et al. | |
| 2005/0014201 | A1 * | 1/2005 | Deuthsch | 435/7.2 |
| 2006/0163463 | A1 * | 7/2006 | Grier | 250/251 |
| 2007/0251543 | A1 * | 11/2007 | Singh | 134/1 |
| 2009/0190221 | A1 * | 7/2009 | Boer et al. | 359/558 |
| 2010/0200739 | A1 * | 8/2010 | Anderson et al. | 250/251 |
| 2010/0207016 | A1 * | 8/2010 | McBride et al. | 250/251 |

FOREIGN PATENT DOCUMENTS

| | | |
|---|---|---|
| GB | 2 408 587 | 6/2005 |
| WO | WO 03/065774 | 8/2003 |
| WO | WO 2005/096115 | 10/2005 |
| WO | WO 2007/042989 | 4/2007 |

OTHER PUBLICATIONS

International Search Report mailed Feb. 13, 2009 in PCT/IB2007/052955.
Written Opinion mailed Feb. 13, 2009 in PCT/IB2007/052955.
Davidson, N. et al, *Optics Letters*, vol. 29, No. 12, Jun. 15, 2004, p. 1318-1320, XP002512949, "High-numerical-aperture focusing of radially polarized doughnut beams with a parabolic mirror and a flat diffractive lens."
Moktadir, A., et al, *J. Micromech. Microeng.*, vol. 14, No. 9, (2004) S82-S85, XP020069767.

* cited by examiner

*Primary Examiner* — Bernard E Souw
(74) *Attorney, Agent, or Firm* — Nixon & Vanderhye P.C.

(57) ABSTRACT

The invention relates to an optical tweezer device including at least one light source and one three-dimensional optical trap, said optical trap comprising one focusing micro-mirror which is adapted to reflect and focus at least a portion of the light emitted by said light source.

24 Claims, 9 Drawing Sheets

(a) (b) (c)

MINIATURIZED OPTICAL TWEEZERS BASED ON HIGH-NA MICRO-MIRRORS

This application is the U.S. national phase of International Application No. PCT/IB2007/052955 filed 25 Jul. 2007 which designated the U.S. and claims priority to International Application No. PCT/IB2006/052567 filed 26 Jul. 2006, the entire contents of each of which are hereby incorporated by reference.

1 TECHNICAL FIELD

The present invention relates to trapping of micrometer-sized dielectric particles, including biological particles, using electromagnetic fields created by strongly focused light.

2 BACKGROUND OF THE INVENTION

In 1970, Arthur Ashkin [1] demonstrated how milliwatts of laser radiation can be used to accelerate end even trap micron-sized particles suspended in liquid and gas. Historically, the first laser trap was relying on two counter-propagating laser beams. Later, Ashkin [2] demonstrated that by focusing a single laser beam very tightly, transparent dielectric particles characterized by a refractive index higher than the refractive index of the surrounding medium could be spatially confined in three-dimensions (3D trapping) near the focus of this single laser beam. The term optical tweezers (or laser tweezers) was coined to define this 3D optical trap relying on a highly focused single laser beam.

When a dielectric particle is located in the electromagnetic field of a laser beam, it experiences two types of forces: a gradient force, attracting the particle towards the region of highest electric field intensity, and a scattering force, acting on the particle in the light propagation direction. In an optical tweezers, in order to create a stable axial equilibrium position close to the beam focus, the gradient force has to overcome the scattering force. The ratio of these two forces depends on the degree of focusing of the laser beam, and a stable equilibrium position in 3D can be created provided that the laser beam is focused with a NA exceeding 0.75. Such a tight focusing is commonly achieved by directing the laser beam through an objective lens with high numerical aperture (NA). 3D trapping can already be achieved if the NA of the objective lens exceeds 0.75. However, in order to maximize the trapping performance of the optical tweezers, objectives with NA>1 are usually employed.

Typical examples of particles that can be trapped are transparent micrometer sized dielectric particles (e.g. polystyrene or silica particles), nanometer sized metallic particles, as well as living biological cells [3] and even neutral atoms. The particles are commonly immersed in a fluid medium whose refractive index is lower than that of the particle itself (water very often). For trapping biological particles the wavelength of the trapping light is typically selected in the near infrared range, where the low absorption coefficient of water, cells and cell constituents avoids damaging the trapped biological particles. Recent progress in the area of micro-fluidics has added a new dimension to the development of optical traps. Controlled handling of tiny quantities of liquids e.g. for lab-on-a-chip devices, may prove beneficial in the development of miniaturized bio-chemical reaction chambers. In this context, large arrays of optical traps may allow investigating parallel and simultaneous (bio)chemical reactions on free-floating arrays of (bio)chemical objects—such as cells, cell fragments, nano-containers, or surface-functionalized beads—for drug screening, sorting, recovery of rare primary cells or assessing statistical data on bio-reactions simultaneously taking place in large ensembles of animal cells, bacteria or vesicles. Optical trapping is fully compatible with standard optical diagnosis techniques, such as fluorescence labelling, fluorescence lifetime imaging (FLIM), fluorescence resonant energy transfer (FRET) or Raman spectroscopy.

In this context, trapping in 3D is important for immobilizing biological objects without contact to the surfaces; artifacts often induced by surface immobilization are excluded and sticking of particles is avoided, allowing the particles to be released simply by turning off the trapping laser. Another important advantage of optical tweezers is that particles are trapped at the observing plane of the objective lens. Therefore, as particles are optically trapped, they naturally lie in the ideal position for observation through the microscope. Moreover, the high-NA of the objective lens allows imaging the particles with high spatial resolution, and if the particles or their constituents are labelled with fluorescent markers, the emitted fluorescence light is collected with high efficiency.

By directing multiple laser beams through the same high-NA objective lens, arrays of laser tweezers have readily been demonstrated relying on different techniques, including diffractive elements [6], VCSEL arrays [7] or microlens arrays [11]. Certain optical trapping schemes even allow generating multiple traps that are computer-reconfigurable by laser scanning [10] or spatial light modulators [9]. However, these approaches suffer from certain limitations, the most important one being that the number of objects that can be trapped simultaneously is limited by the field of view of the focusing objective lens. An objective lens characterized by NA=1.25 has a field of view diameter in the order of 200 μm. When trapping living cells having typical sizes of 10-15 μm, this roughly means that no more than 50 cells may be trapped and observed simultaneously. Also, high-NA objective lenses are bulky, expensive, and their extremely short working distance is a restricting factor to the use of optical tweezers in many fields.

A highly non-conventional approach for creating arrays of optical traps would consist in using arrays of micro-optical elements. Provided that each of these micro-optical elements may generate its own optical trap, the number of traps may be increased at will simply by increasing the number of the said micro-optical elements. Another particular advantage of such an approach would be that the micro-optical elements may be mass produced in a parallel fashion using micro-fabrication techniques and also replicated by, e.g. mold casting approaches, to reach extremely low production costs. However, despite the efforts in the micro-optics field for improving the performance of refractive or diffractive micro-lenses, those are still restricted by technological as well as physical limits to relatively low numerical apertures (NA=0.5), meaning that they can not be employed for 3D optical trapping. Although air-immersed two-sided aspheric refractive lenses with NAs as high as 0.7 are commercially available, such a high NA can not be reached with microlenses [8]. For instance, refractive microlenses are commonly manufactured on one side of glass substrate, i.e. they are small plano-convex lenses. Simple calculations show that, for reaching high NAs, the sides of a single-sided aspherical microlens should be very steep relative to the substrate if standard optical glass (n=1.5) is used. Besides the technical issues related to the fabrication of such high aspect-ratio aspherical microlenses, their effective numerical aperture is limited because the steep incidence angles strongly restrict the fraction of light which is effectively refracted at the higher NAs. On the other hand, high-index materials, e.g. silicon, are not employable in the visible and near-infrared ranges due to their poor optical transmission at these wavelengths. Diffractive microlenses (e.g. Fresnel microlenses) also are limited to NAs insufficient for generating optical tweezers, both because of the limited resolution of the manufacturing processes, and because of the rapidly decreasing diffraction efficiency at small grating periods. Finally, graded-index (GRIN) microlens arrays may also be considered, but their NA is typically limited to 0.5, this being related to the technical difficulties in creating very high refractive index gradients within the bulk materials (currently, the best technology seems to be based on silver-ions exchange).

These are essentially the reasons why objective lenses are still conventionally used for optical tweezers. Only a few examples of miniaturized devices capable of generating 3D optical traps without an objective lens have been demonstrated [4, 5]. These systems take advantage of a dual-beam trap [1] configuration (either using two facing optical fibers, or two facing semiconductor lasers) therefore they are relying on a principle different than optical tweezers (which is a single-beam optical trap). However, these approaches are limited to trapping a restricted number of particles; they are unadapted for generating large arrays of optical traps.

3 PRIOR ART

The following prior art systems relates to devices that do not require a high-NA objective lens for optical trapping. However, not all of these systems can generate 3D traps; very often, particles are pushed toward a surface and the optical confinement is only two-dimensional. In a general manner, systems that allow creating very large arrays of optical traps cannot generate 3D optical trapping. On the other hand, systems that achieve 3D optical confinement (in a counter-propagating two-beam trap configuration) are restricted in the number of traps they can generate.

In U.S. Pat. No. 6,991,939 (Walt et et al.) an apparatus for multiple optical trapping is disclosed. The apparatus uses an array of optical fibers (fiber bundle) parceling a beam of light into individual beams of light, the distal end of each fiber being light focusing, or the fibers being based on GRIN (graded-index) technology. The main limitation of this system is that the NA of the distal end of the fibers is insufficient for generating optical tweezers, thus the system is limited to 2D trapping.

In US 2004/0256542 (Okazaki) a device for multiple optical trapping is described, essentially taking advantage of a digital micro-mirror device (DMD) in combination with an array of optical fibers, the distal end of each fiber being light focusing to generate the optical traps. This system, as the preceding one, cannot achieve 3D trapping because of the limited NA of the fibers.

In WO 2005112042 (Dholakia et al.) a micro-fluidic device integrating semi-conductor lasers for creating optical traps is disclosed. The device is claimed to be manufactured using a semiconductor material, wherein fluidic channels and the semiconductor lasers are defined inside the said material. The system uses a dual-beam trap configuration from two facing semiconductor lasers to generate 3D optical traps. However, large arrays of 3D traps can presumably not be generated with this system.

In US 2005/0146794 (Menon et al.) a system for optically manipulating micro-particles using an array of focusing elements is disclosed. The system is claimed to use a multiplexing module, such as a digital micro-mirror device (DMD), or an array of semiconductor lasers. However, the array of focusing elements is claimed to be composed of diffractive and/or refractive micro-optical elements. These focusing elements cannot achieve the high-NA necessary for generating optical tweezers. Thus the system is limited to 2D optical trapping.

The device described in WO 200209483 (Ozkan et al.) may be considered to be relevant because it employs VCSEL diodes (Vertical Cavity Surface Emitting Lasers) for optical trapping. The apparatus involves the use of a multitude of (VCSEL) whose focused laser radiation is used to manipulate multiple objects at the same time, or to focus multiple beams onto a potentially quite large object in order to exert more optical force on the object. However, the system still relies on an objective lens to focus the laser radiation from the multiple VCSELs tightly enough to generate 3D traps.

Finally, mirrors in the context of optical trapping have been proposed by Zemanek [12]. However, this work discloses the provision of a flat reflective element located opposite a focalizing element (an objective lens), to increase the performance of a 3D optical tweezers. A standing wave phenomenon is generated, characterized by extremely sharp light intensity modulations arising from the interference between the forward and the backward (reflected) laser beam. Such a phenomenon may indeed by used to create 3D traps with lower NA optics, but is only applicable to extremely small particles, typically much smaller than the wavelength of the trapping laser. Multiple traps were not demonstrated and probably cannot be generated with such a system.

4 SUMMARY OF THE INVENTION

The present invention is based on the use of at least one reflective focusing micro-mirror capable of high numerical aperture focusing. As it will be shown below, its characteristics make it an ideal solution for integrating optical traps at a chip-level and for creating massively parallel two dimensional arrays of optical tweezers in advanced bio-analytical systems.

In the present text, the expression "micro-mirror" has to be understood as a mirror with a cross sectional diameter less than 1 mm, generally less than 500 micrometers.

In the present invention, preferably an array of focusing high-NA micro-mirrors is used to generate an array of optical tweezers, with no need for high-NA objective lenses as in conventional optical tweezers. Thanks to the high achievable NA, each micro-mirror is capable of focusing the light so tightly and with such a low level of aberration that an array of three dimensional single-beam optical traps (optical tweezers) is created, with no need for any microscope objective lens.

Miniaturizing such micro-mirrors and arranging them in two dimensional arrays allows creating virtually unlimitedly large optical traps arrays that could be integrated in more complex micro-devices, including micro-fluidic devices.

In addition, since the particles are trapped at the focus of the micro-mirrors, each micro-mirror of the array can be used for the parallel imaging and/or high-NA light-signals collection simultaneously from all the trapped particles.

Three dimensional trapping, miniaturization, massive parallelism, and highly-efficient light-signals collection make the present invention an ideal solution for integrating arrays of optical traps into advanced bio-analytical miniaturized systems.

5 BRIEF DESCRIPTION OF THE DRAWINGS

FIG. 1 compares the focusing geometry of a single plano-convex lens with the focusing geometry of air-immersed and solid immersed micro-mirrors.

FIG. 2 compares the achievable numerical aperture of parabolic mirrors with that of a single plano-convex lens, as a function of the ratio cross sectional diameter ($d=2r_{max}$) over radius-of-curvature (R).

Figure 8:
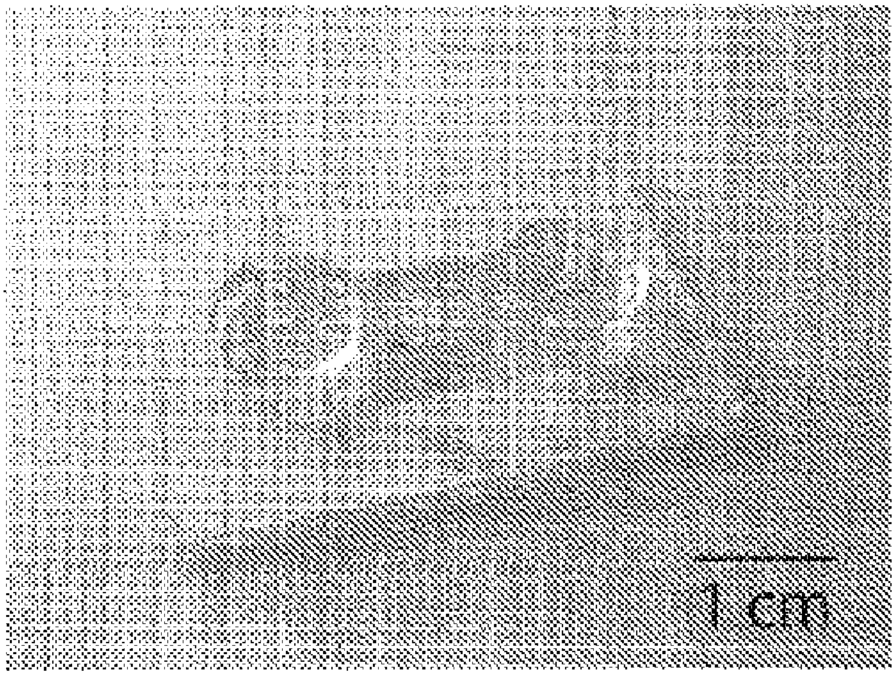

FIG. 8: picture of an experimental micro-fluidic device embedding a micro-mirror array.

Figure 9:
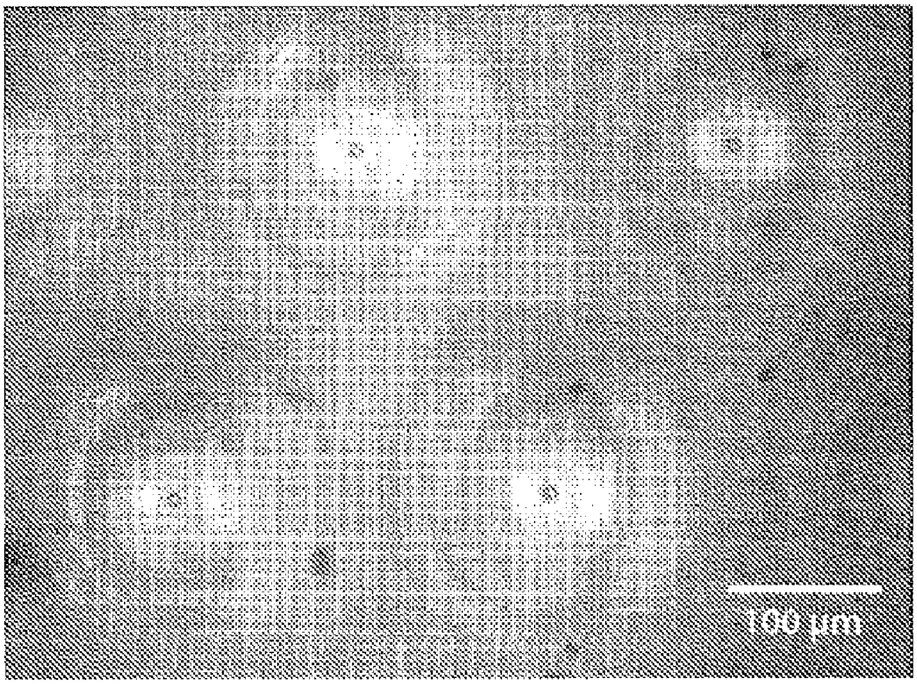

FIG. 9: picture showing 4 polystyrene beads 9.33 μm in diameter optically trapped in three dimensions at the focus of parabolic micro-mirrors.

Figure 10:
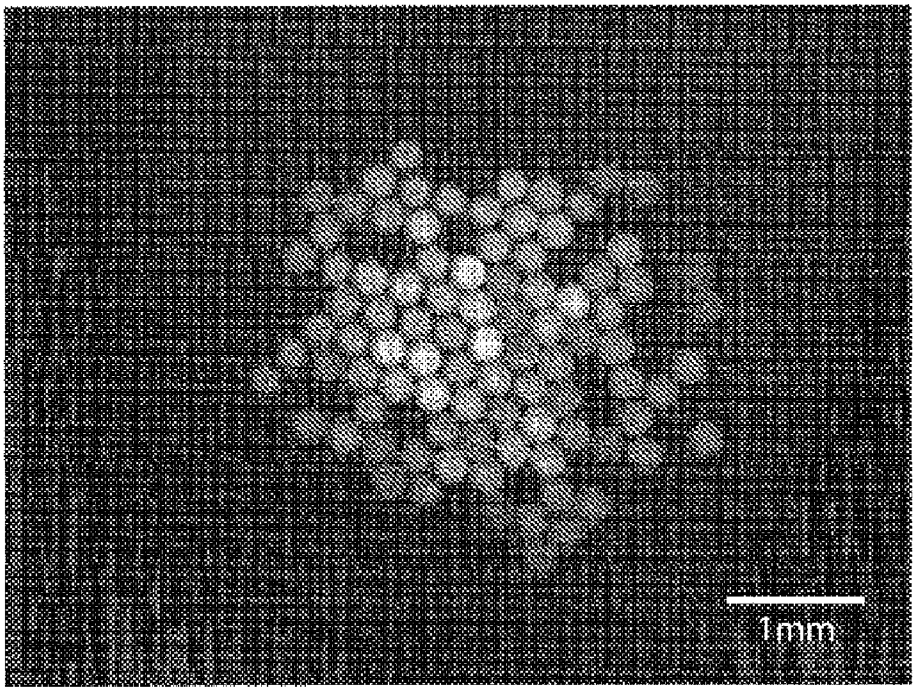

FIG. 10: picture illustrating the fluorescence light collection with an array of micro-mirrors. The mirrors "turn-on" as particles progressively fill the array of optical traps, revealing the particle's individual fluorescence light color.

6 DETAILED DESCRIPTION OF THE INVENTION

6.1 Micro-mirrors as High-NA Micro-optical Components

The core of the present invention lies in the use of reflective instead of refractive or diffractive micro-optical components. While refractive and diffractive focusing micro-optical components can only achieve relatively limited numerical apertures (typically NA<0.5), reflective focusing micro-mirrors easily allow reaching very high NAs.

The micro-mirror arrays as defined in a preferred embodiment of the present invention should not be confused with electrostatically actuated micro-mirror arrays (also known as digital micro-mirror devices, DMDs). Electrostatically actuated micro-mirror arrays are composed of a matrix of flat, independently actuated tilting micro-mirrors. These are typically employed for spatially and temporally modulating a light source. In contrast, the invention embodiment below describes a fixed array of concave micro-mirrors, each micro-mirror being employed for focusing a portion of an incident electromagnetic radiation, similarly as a microlens array.

The fact that focusing mirrors can be used to focus light at high-NA is not new by itself. For example, a parabolic mirror focuses a plane wave traveling along the optical axis to one point without aberrations in the geometrical optics approximation, and in this sense it is an ideal focusing device. Nevertheless, parabolic mirrors are not very frequent for microscopy and imaging because slight deviations of the incident beam from the optical axis or from parallelism give rise to huge aberrations, especially for a high-NA mirror, resulting in a very small field of view. The classical imaging devices for microscopy are objective lenses (being a system composed of multiple lenses) that provide an excellent resolution all over a wide field of view resulting from the high degree of aberration correction combined with the high achievable NA.

Optical tweezers using focusing mirrors have never been proposed. The reason is very likely to be related both to their very restricted field-of-view, especially if characterized by a high-NA, and to the fact that the object and image spaces of a focusing mirror both are located on the same side of the mirror, which is very unpractical in most applications. Essentially, a macroscopic focusing mirror would not have any advantage, but rather many disadvantages over a high-NA objective lens. The innovation lies in the fact that miniaturized focusing mirrors can be used as high-NA micro-optical components, and therefore they offer a unique opportunity for generating 3D optical traps with micro-optical components. Moreover, high-NA miniaturized mirrors can be very easily fabricated, e.g. simply by molding state-of-the-art low-NA refractive microlenses.

Figure 1:
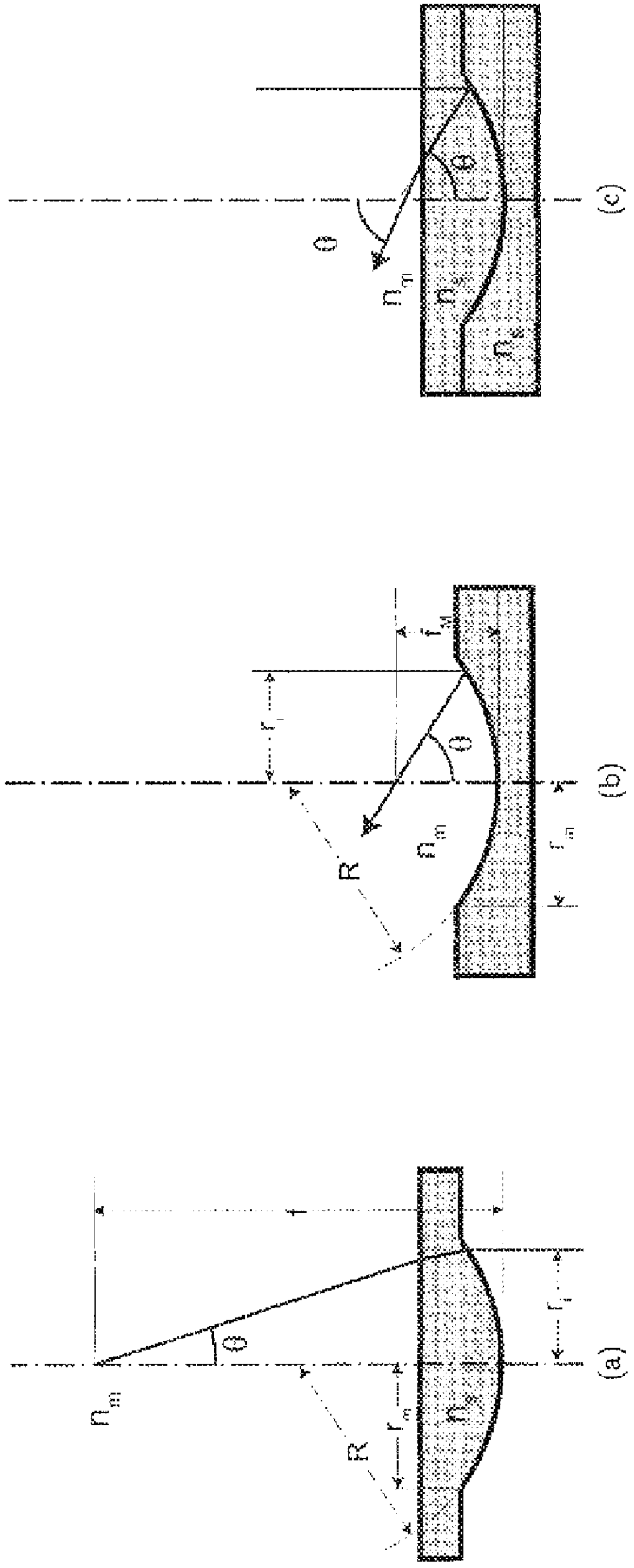

It is not obvious at first glance that, when compared to lenses, focusing mirrors with very modest curvatures can already offer extremely high NAs. Indeed, because the light focusing process is reflective rather than refractive, a miniaturized focusing mirror has a four to six times higher NA than a refractive microlens characterized by the same geometry. This is illustrated in FIG. 1, where the focusing geometry of a single plano-convex lens is compared with the focusing geometry of an air-immersed and solid-immersed focusing, concave micro-mirror. Let us first introduce the reasoning in a paraxial approximation, where the definition of the numerical aperture $NA=n_m \sin\theta_{max}$ simplifies to $NA \approx n_m \theta_{max}$.

FIG. 1*a* illustrates the focusing geometry of a single plano-convex lens, characterized by its cross-sectional radius $r_{max}$, its radius-of-curvature R, and the refractive index $n_s$ of the substrate material composing the lens. The focal length of a plano-convex lens is approximately given by $f_L \approx R/(n_s-1)$. A ray hitting the surface of a plano-convex lens at a distance $r_i$ ($r_i \leqq r_{max}$) from the optical axis will be refracted at an angle $\theta=r_i/f_L$. Therefore, in a paraxial approximation, the numerical aperture $NA_L \approx r_{max}/f_L$ of the lens is given by $$NA_L \approx (n_s-1)r_{max}/R \quad (1)$$

FIG. 1*b* illustrates a concave mirror, characterized by the same radius-of-curvature R and the same cross-sectional radius $r_{max}$ of the plano-convex lens of FIG. 1*a*. The mirror allows achieving a much higher NA than the plano convex lens. Indeed, a ray hitting the reflecting surface of the mirror (at the same distance $r_i$ from the optical axis as that specified for the plano-convex lens) is deviated at larger angles θ than in the refractive process taking place in previously described plano-convex lens. The rays are reflected at an angle $\theta=r_i/f_M$, similarly as in the case of the lens. However, the focal length of the mirror is given by $f_M=R/2$ (which happens to be typically much smaller than fL). In a paraxial approximation, the numerical aperture $NA_M \approx r_{max}/f_M$ of the focusing mirror can be expressed as $$NA_M \approx 2n_m r_{max}/R \quad (2)$$

Therefore, the ratio of NAs between a focusing mirror and a plano-convex lens characterized by the same geometry (same $r_{max}$ and R) is given by $$NA_M/NA_L \approx 2n_m/n_s-1 \quad (3)$$

If the mirror is immersed in air ($n_m=1$), and supposing that the plano-convex lens is composed of a standard optical glass characterized by $n_s=10.5$, the ratio of NAs equals to four, i.e. numerical aperture of the mirror is four times higher than that of the plano-convex lens.

If the mirror is immersed in water ($n_m$=1.33) rather than in air, the NAs ratio reaches 5.33. Indeed, the reflection angle θ is independent on the refractive index $n_m$, but due to the high refractive index $n_s$, the numerical aperture NA≈$n_s$θ is increased.

FIG. 1*c* illustrates how the NA of the mirrors can further be increased by immersing the mirror in a glass substrate characterized by a relatively high refractive index $n_s$ ($n_s$>$n_m$). Again, the reflection angle θ is unchanged, but because of the high refractive index $n_s$, the numerical aperture NA≈$n_s$θ is increased with respect to the NA of an air or water-immersed mirror. As the ray crosses the interface (passing from $n_s$ to $n_m$), the angle between the ray and the optical axis changes from θ to θ'. But the NA is maintained at the higher value imposed by the high refractive index substrate, which is simply a consequence of the definition of the numerical aperture and Snell's law. Practically, if the substrate is characterized by $n_s$=10.5 (standard optical glass), the ratio of NAs is equal to six. Therefore, in the paraxial approximation, the solid-immersed mirror of FIG. 1*c* has a six times higher NA than the plano-convex lens illustrated in FIG. 1*a*, although their cross-sectional radius $r_{max}$ and radius-of-curvature R are strictly the same.

Figure 2:
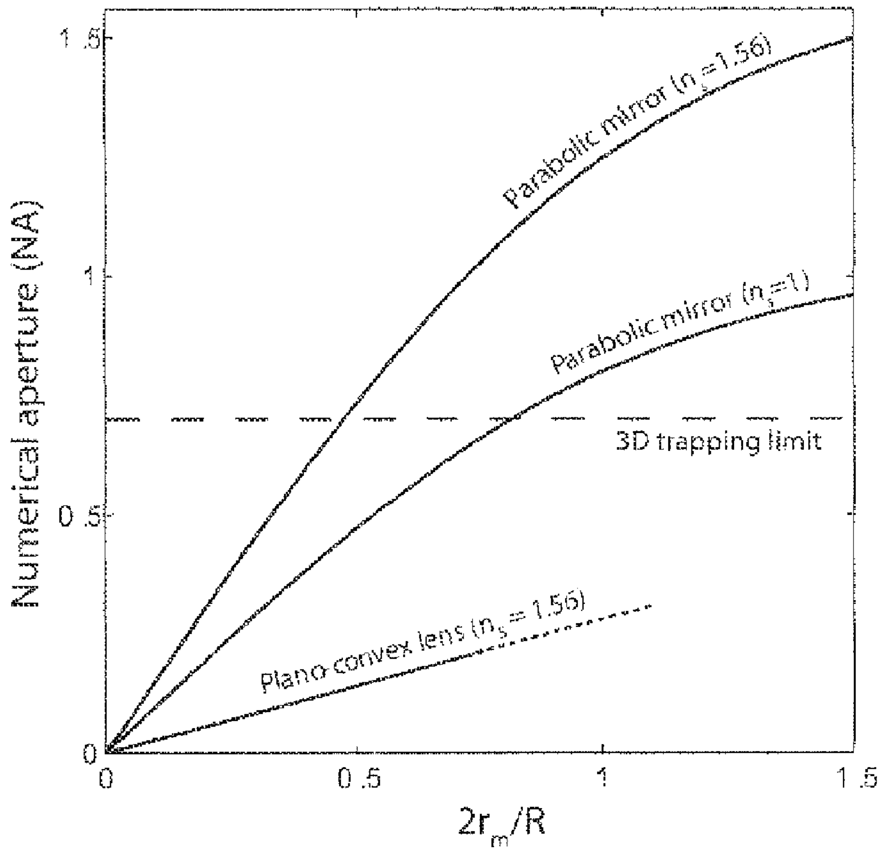

The paraxial approximation for the NA is reasonable when considering plano-convex lenses typically characterized by numerical apertures not exceeding $NA_L$≈0.2. However, such paraxial considerations do not apply any longer for high-NA focusing mirrors. Also, if the focusing geometry of FIG. 1*b* or FIG. 1*c* are employed (where the incoming laser radiation is a plane wave) the mirror cross-sectional profile should ideally be parabolic to achieve aberration-free focusing (a spherical mirror would produce spherical aberration in this case). The numerical aperture of a parabolic mirror $NA_{PM}$ is exactly given by $$NA_{PM}=n\sin[2\arctan(r_{max}/R)] \quad (4)$$

where n may either be equal to $n_s$ or $n_m$, depending if the mirror is immersed in a high refractive index substrate or not. Equation (4) still holds for parabolic mirrors characterized by high-NA. FIG. 2 graphically compares the numerical apertures of a single plano-convex lens (paraxial approximation) with the numerical apertures achievable with parabolic micro-mirrors (equation (4)), as a function of their diameter d=2$r_{max}$ to radius-of-curvature R ratio. The lens is composed of a substrate characterized by an index of refraction $n_s$=1.56 (continuous line ending in dots, paraxial approximation). The comparison is made with an air-immersed ($n_m$=1) as well as a solid-immersed ($n_s$=10.56) parabolic mirror. The lower-limit numerical aperture for three dimensional optical trapping (NA≈0.75, horizontal dashed line) is also represented. In the non-paraxial regime, the NAs ratio between the parabolic mirror and the plano-convex lens is somewhat reduced with respect to what deduced from the paraxial approximations (due to the non-linearity of equation (4)), but still exceeds five for solid-immersed mirrors in many practical cases.

6.2 Optical Trapping with Micro-mirrors

An array of miniaturized focusing mirrors may be used to create large arrays of optical tweezers. This approach offers several advantages, the most important one being that the total number of traps that can be generated with an array of micro-mirrors is not limited by the small field of view of a high-NA objective lens, as it is the case in conventional optical tweezers. When using an array of micro-mirrors, each trap has its own miniaturized focusing element, thus the size of the array may be increased at will and the numerical aperture can be chosen independently of the cross-sectional diameter of the mirrors.

Moreover, an optical tweezers generated by a parabolic mirror is even likely to allow for stronger optical trapping forces than an optical tweezers generated by an objective lens having the same numerical aperture. In fact, a light beam focused by a parabolic mirror has proportionally more energy in the peripheral rays (due to its different apodization function), which are known to be of greater importance for the axial trapping characteristics.

In order to achieve optical trapping, each micro-mirror should be sensibly larger in cross sectional diameter than the objects to be optically trapped, to ensure that the trapping light is not blocked or too much perturbed by the object to be trapped before arriving on the mirror. Also, in the purpose of three dimensional optical trapping, the micro-mirrors should be characterized by a high numerical aperture, at least 0.75, but ideally NA>1. The reflecting surface of the micro-mirrors may be composed of a thin metal layer, or a multi-layer deposition of dielectrics (dielectric mirror). This reflecting surface should be highly reflecting for the trapping light wavelength. Other wavelengths may be partly or totally reflected or transmitted, according to the particular application and for the purpose of observation and/or light signals detection.

The actual cross-sectional profile of the micro-mirrors is chosen according to the particular physical configuration, but in a general manner this profile will typically be aspherical.

6.2.1 Parabolic Mirrors

Figure 3:
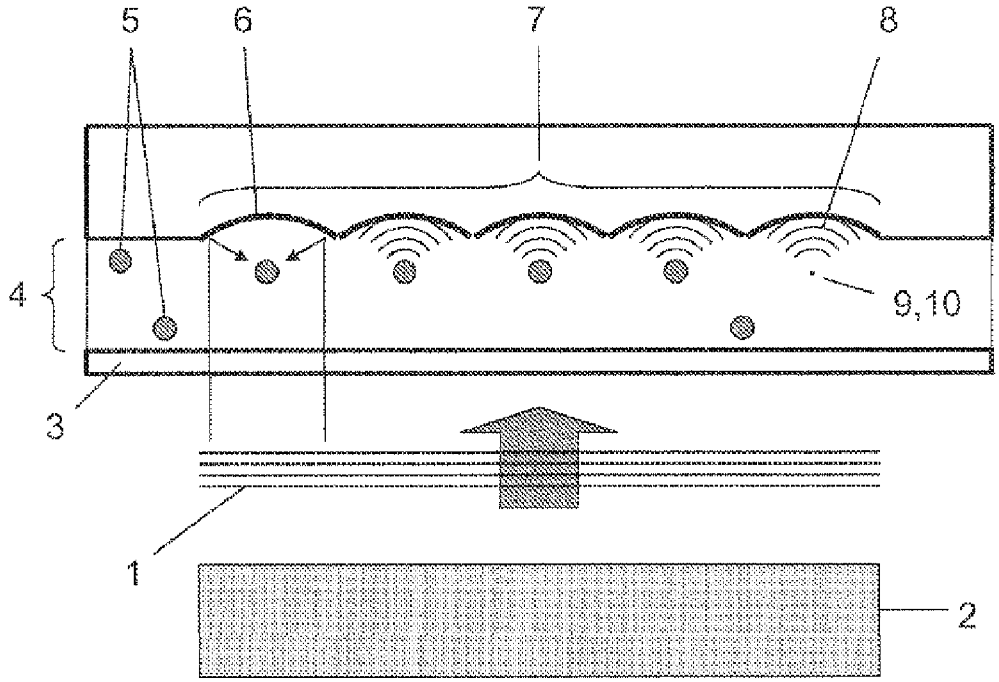
FIG. 3 illustrates a basic embodiment for multiple optical trapping using a focusing parabolic micro-mirror array.

In one embodiment of the invention, the cross-sectional shape of the micro-mirrors is chosen to be parabolic. As illustrated on FIG. 3 a single collimated light beam 1 from a laser source 2 first crosses a clear optical window 3 composing one of the walls of a fluid chamber 4, containing a suspension of dielectric particles 5 to be trapped. The collimated light beam 1 is reflected on the surface 6 of the array of micro-mirrors 7 placed at the opposite side of the fluid chamber, causing the plane wave to be transformed into a multitude of highly converging electromagnetic waves 8. The focus 9 of each of these highly converging waves coincides to an optical tweezers 10. In this case a parabolic profile is chosen because this cross-sectional profile allows the incoming plane wave 1 to be focused with the minimal aberration. Using mirrors with a spherical cross sectional profile would introduce unwanted spherical aberration in the system.

6.2.2 Other Micro-mirror Cross-sectional Profiles

Figure 4:
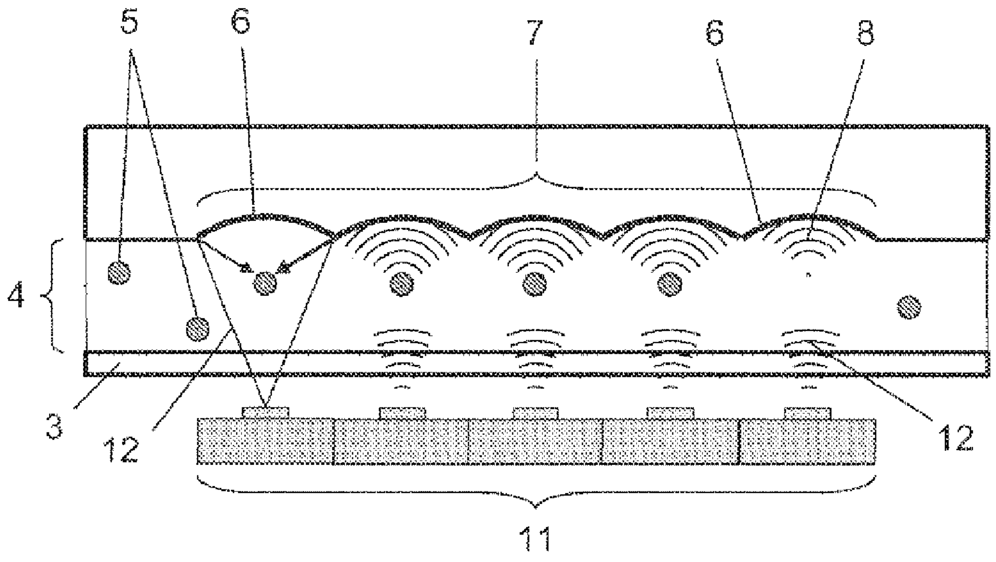
FIG. 4 illustrates another embodiment for multiple optical trapping using an array of focusing micro-mirrors in combination with an array of VCSEL.

Using micro-mirrors with a parabolic cross-sectional profile and a single laser source is one among other possible embodiments of the present invention. FIG. 4 illustrates another possible embodiment, where an array of VCSELs semi-conductor laser diodes 11 (Vertical Cavity Surface Emitting Lasers) is used as a multiple laser light source, producing an array of lightly diverging laser beams 12. These low-NA diverging beams are subsequently transformed into high-NA converging beams 8 by reflection on the surface 6 of the array of micro-mirrors 7, having the same pitch as the VCSEL array. In this situation the ideal cross-sectional profile for the mirrors would be defined by a elliptical profile.

Figure 5:
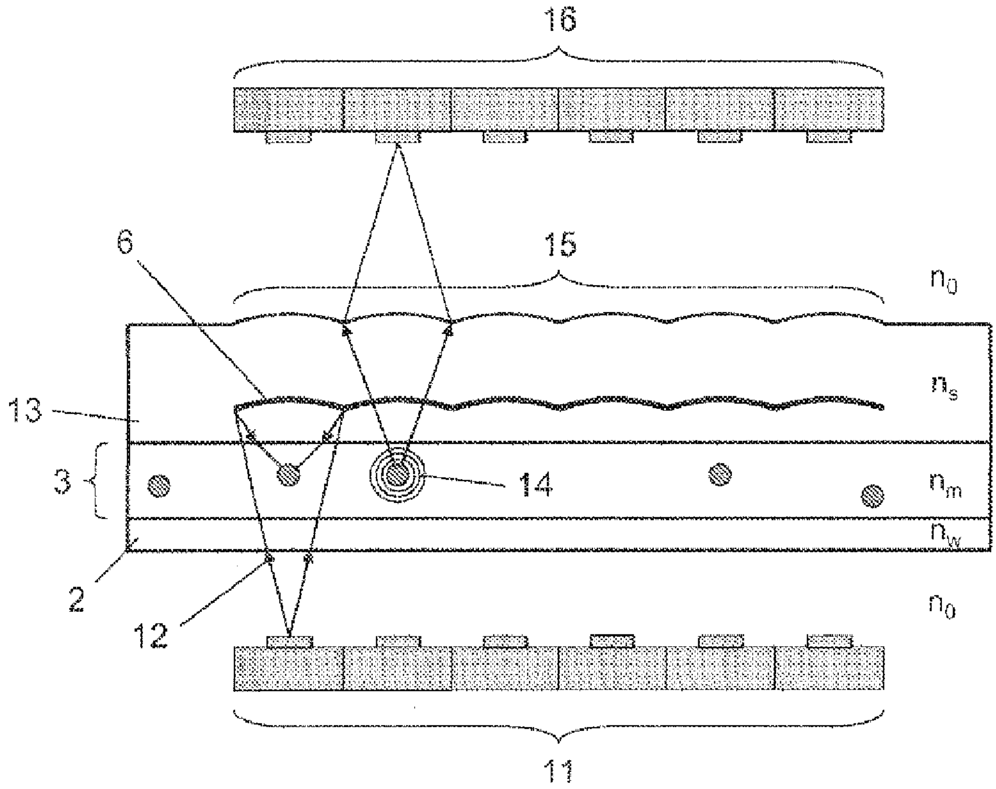
FIG. 5 illustrates another embodiment for multiple optical trapping using an array of focusing micro-mirrors in combination with an array of VCSEL, comprising an additional array of micro-lenses for light-signals collection from the trapped particles.

A somewhat different embodiment is illustrated in FIG. 5. In this case the micro-mirrors 6 are embedded in a substrate 13 characterized by a refractive index nS (similarly as in FIG. 1*c*). The laser beam 12 produced by each VCSEL crosses a multitude of refractive index interfaces ($n_0$→$n_w$→$n_m$→$n_s$) at non-normal incidence before being reflected by the mirror surface 6, and one more interface ($n_s$→$n_m$) after being focused backwards by the mirror. These refractive index interfaces introduce a certain amount of spherical aberration into the optical system. Especially the last interface is introducing a significant level of spherical aberration into the system because of the high convergence of the reflected laser beam, which may cause optical trapping to be less effective or even impossible. A correction to these aberrations can advantageously be integrated in the cross-sectional shape of the micro-mirrors, in order to reach the best possible focused laser beam characteristics for optical trapping. Generally, given the geometrical configuration it is always possible to define an ideal profile for the micro-mirrors, ensuring that the high-NA light focusing is achieved with minimal or no aberrations. This profile will typically be aspherical, although spherical profiles may be used in certain configurations. State-of-the-art micro-optics manufacturing techniques (e.g. fabrication of microlenses by photolithography, resist reflow, followed by reactive ion etching) allow controlling the cross-sectional profiles of refractive microlenses with very high accuracy.

6.3 Observation, light signals detection

Observation or collection of light signals from the trapped particles (e.g fluorescence signals, or Raman spectroscopy) can be achieved using a microscope objective lens, using secondary micro-optics, or taking advantage of the high-NA micro-mirrors.

FIG. 5 illustrates the use of secondary micro-optics for light-signal collection from the trapped particles. The mirrors being embedded into the substrate 13, the refractive index ($n_s$) is equal on both sides of the mirrors. Provided that the reflecting surface 6 of the focusing mirrors is at least partially transparent to wavelengths different than the wavelength of the laser used for optical trapping, part of the light signals 14 emitted by the trapped particles may cross the mirrors without being deflected. Then, a secondary micro-optics 15 (e.g a micro-lens array) can be used to focalize these light signals onto an array of light-detectors 16.

Figure 6:
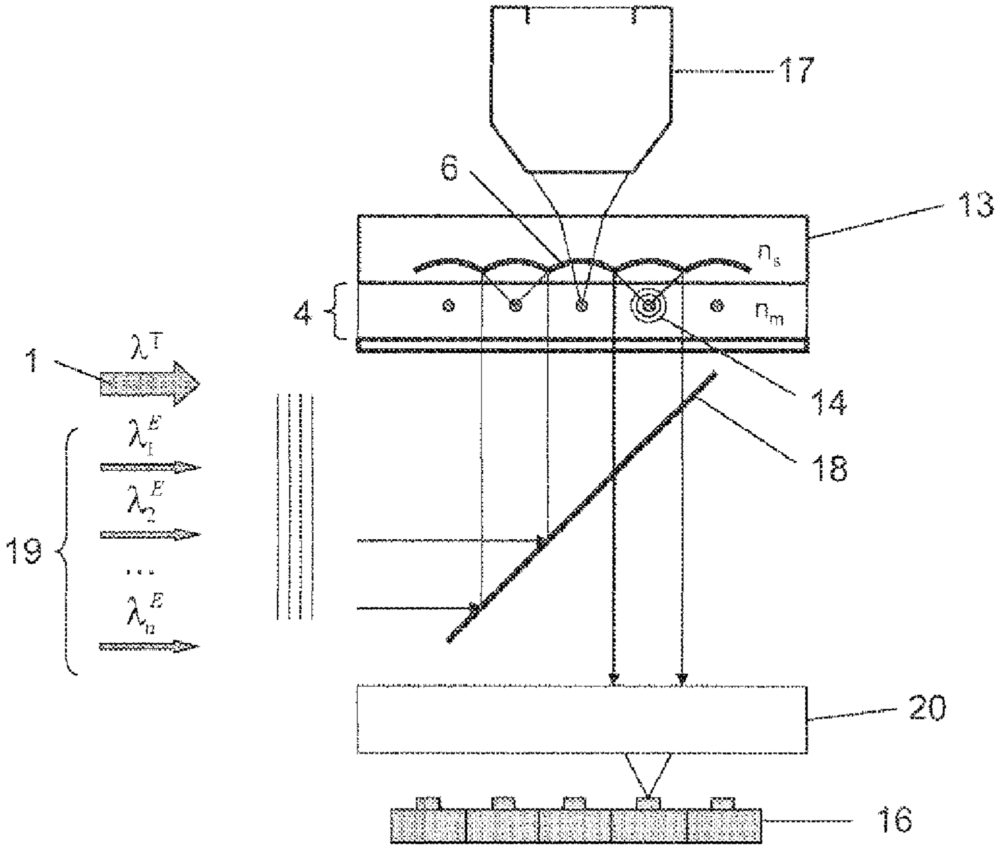
FIG. 6 illustrates how the observation of trapped particles can be performed using a microscope objective, and how high-NA light-signals detection from the trapped particles can be achieved thanks to the micro-mirrors.

As depicted in FIG. 6 an objective lens 17 may also be used to observe the trapped particles across the micro-mirrors 6. Again, the micro-mirrors should be transparent or partly transparent at least to certain light wavelengths other than that of the trapping laser and if the refractive index ($n_s$) is equal on both sides of the micro-mirrors 6, similarly to what already described in FIG. 5, the micro-mirror array would not act as a diverging microlens array. Therefore, an image of the trapping plane may be obtained by observing with a microscope objective across the micro-mirrors.

Under certain circumstances, since the particles are trapped very close to the focus of the micro-mirrors, each micro-mirror can be used to image the particle that is trapped at its focus, or collect light signals (e.g. fluorescence signals) from the particles very efficiently because of the high-NA of the mirror.

As illustrated on FIG. 6 more excitation laser sources and produced laser beams 19 characterized by different wavelengths $\lambda_1, \ldots \lambda_m$, (or a broadband light source used in combination with excitation filters) can be coupled with the trapping laser light 1 (of wavelength $\lambda_T$), reflected on a wavelength-selective flat mirror 18 and focused by the mirrors onto the particles together with the trapping light. Subsequently, light-signals 14 emitted by the trapped particles are collected by the mirrors and transmitted through the wavelength selective flat mirror 18 (which should thus be transparent to the emitted light signals) to a light detector array 16, eventually through an imaging system 20. This mode of operation can be advantageously used for fluorescence excitation on the trapped particles, or Raman spectroscopy.

6.4 Integration into Micro-fluidics

Figure 7:
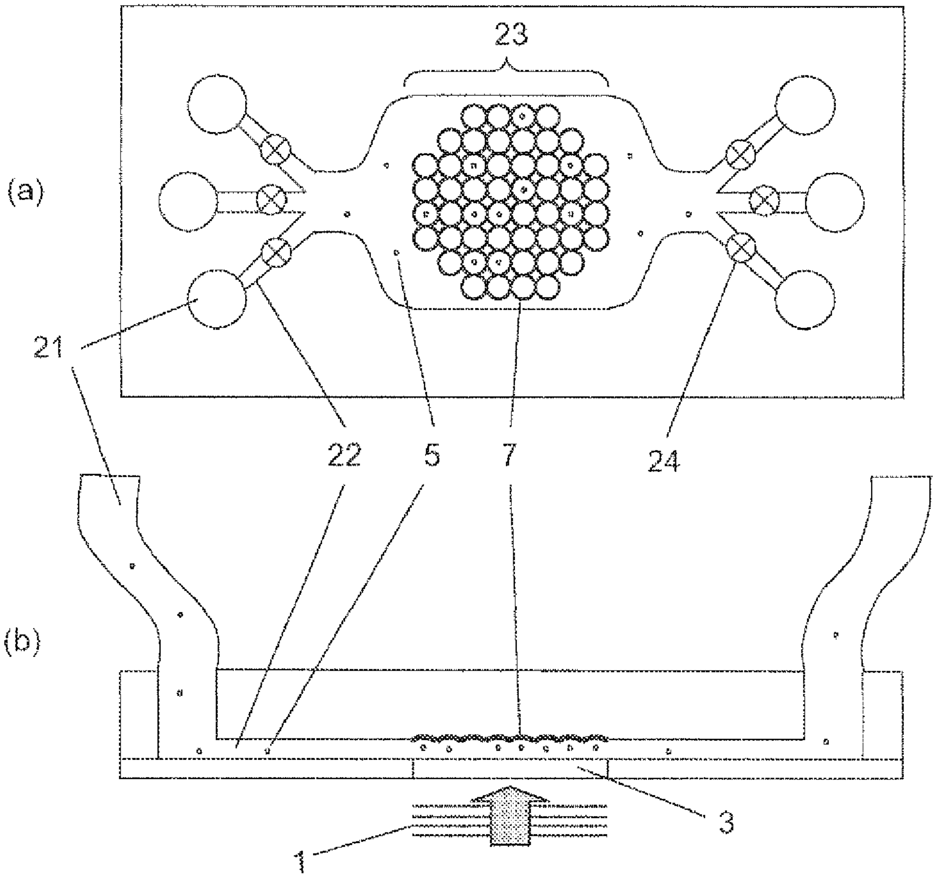
FIG. 7 illustrates an example of how the micro-mirrors array can be integrated within a micro-fluidic device to generate multiple optical tweezers within the micro-fluidic device.

The present invention is particularly well suited for integrating 2D arrays of optical tweezers into micro-fluidic systems. A micro-mirror array can be directly integrated onto a micro-fluidics device. FIG. 7 illustrates a top (a) and side (b) view of a micro-fluidic device integrating a micro-mirror array for optical trapping. The micro-fluidic system comprises inlets 21 for supplying both fluids containing particles 5 to be trapped and analyzed and fluids containing (bio) chemical reagents or molecules. The micro-fluidic device also comprises micro-channels 22 to guide these fluids to the trapping area 23 where the micro-mirrors 6 are located. The micro-fluidic system may also comprise valves 24 to switch among the different fluids, and mixing chambers, and micro-pumps, and the like. The wall of the fluidic channel should locally consist of a clear, optically flat window 3, at an appropriate position to allow for the trapping laser light to reach the micro-mirror array, and to allow for light signals to reach external detectors. It is thus sufficient to shine a collimated light beam 1 onto the portion of the micro-fluidic chip where the micro-mirrors are integrated to obtain an array of optical tweezers within the microfluidic device.

7 PROOF OF PRINCIPLE

An array of parabolic micro-mirrors was successfully produced by negative replication of a commercially available array of micro-lenses in UV-hardening photo-resist deposited on a glass substrate. The reflective surface consisted of a thin (60 nm) layer of gold, which is highly reflecting for the used trapping laser wavelength ($\lambda$=1064 nm) and partially transmitting in the visible range. The micro-mirrors were subsequently embedded in an additional UV-hardening photo resist and covered by a 80 μm thick cover-glass. The produced micro-mirrors have a cross sectional diameter of 245 μm, and a numerical aperture of NA=0.96.

FIG. 8 is a picture of a simple fluidic device embedding the above described micro-mirrors. The construction is similar to what described in FIG. 7, except that only a single micro-fluidic channel is present (only one fluid inlet and one fluid outlet). FIG. 9 shows a transmission micrograph of four polystyrene beads 9.33 μm in diameter being trapped at the focus of four different micro-mirrors. Thanks to the high NA of the micro-mirrors three dimensional trapping could be achieved. The traps could keep particles in position a flow speeds exceeding 350 μm/s with optical powers of 34 mW per trap. This trapping performance is comparable to that of optical tweezers generated using high-NA objective lenses. Finally, FIG. 10 is an image of the plane of the micro-mirror taken while multiple fluorescent polystyrene particles (6 μm in diameter) are trapped within the multiple optical tweezers generated by the micro-mirrors. He—Ne lasers were used to induce fluorescence emission from the particles, with an embodiment similar to that described in FIG. 6.

REFERENCES

[1] A. Ashkin. Acceleration and trapping of particles by radiation pressure. *Phys. Rev. Lett.,* 24:156, 1970.

[2] A. Ashkin, J. M. Dziedzic, J. E. Bjorkholm, and S. Chu. Observation of a single-beam gradient force optical trap for dielectric particles. *Opt. Lett.,* 11:288-290, 1986.

[3] A. Ashkin, J. M. Dziedzic, and T. Yamane. Optical trapping and manipulation of single cells using infrared-laser beams. *Nature,* 330:769-771, 1987.

[4] A. Constable, J. Kim, J. Mervis, F. Zarinetchi, and M. Prentiss. Demonstration of a fiberoptic light-force trap. *Opt. Lett.,* 18:1867-1869, 1993.

[5] S. J. Cran-McGreehin, K. Dholakia, and T. F. Krauss. Monolithic integration of microfluidic channels and semiconductor lasers. *Opt. Express,* 14:7723-7729, 2006.

[6] E. R. Dufresne and D. G. Grier. Optical tweezer arrays and optical substrates created with diffractive optics. *Rev. Sci. Instrum.,* 69:1974-1977, 1998.

[7] Y. Ogura, K. Kagawa, and J. Tanida. Optical manipulation of microscopic objects by means of vertical-cavity surface-emitting laser array sources. *Appl. Opt.,* 40:5430-5435, 2001.

[8] H. Ottevaere, R. Cox, H. P. Herzig, T. Miyashita, K. Naessens, M. Taghizadeh, R. Volkel, H. J. Woo, and H. Thienpont. Comparing glass and plastic refractive microlenses fabricated with different technologies. *J. Opt. A—Pure Appl. Op.,* 8:S407-S429, 2006.

[9] M. Reicherter, T. Haist, E. U. Wagemann, and H. J. Tiziani. Optical particle trapping with computer-generated holograms written on a liquid-crystal display. Opt. Lett., 24:608-610, 1999.

[10] K. Sasaki, M. Koshioka, H. Misawa, N. Kitamura, and H. Masuhara. Pattern-formation and flow-control of fine particles by laser-scanning micromanipulation. *Opt. Lett.,* 16:1463-1465, 1991.

[11] C. H. Sow, A. A. Bettiol, Y. Y. G. Lee, F. C. Cheong, C. T. Lim, and F. Watt. Multiple-spot optical tweezers created with microlens arrays fabricated by proton beam writing. *Appl. Phys. B,* 78:705-709, 2004.

[12] P. Zemanek, A. Jonas, L. Sramek, and M. Liska. Optical trapping of rayleigh particles using a gaussian standing wave. *Opt. Commun.,* 151:273-285, 1998.

The invention claimed is:

1. An optical tweezer device including at least one light source and one three-dimensional optical trap, said optical trap comprising one focusing micro-mirror which is adapted to reflect and focus at least a portion of the light emitted by said light source.

2. The device according to claim 1 wherein said focusing mirror has a numerical aperture equal to or exceeding 0.8.

3. The device according to claim 1 wherein the axially symmetric cross-sectional profile of the said focusing mirror is selected among (a) Spherical (b) Parabolic (c) Elliptic (d) Hyperbolic (e) any other aspherical cross-sectional profile, optimizing the focusing properties of the mirror to the particular geometrical/physical configuration.

4. The device according to claim 1 comprising several focusing mirrors arranged into a 1D or 2D arrays.

5. The device according to claim 4 wherein said mirrors are designed to highly reflect the light wavelength used for trapping and partially or totally transmit or reflect other wavelengths.

6. The device according to claim 1 wherein said focusing mirror(s) is/are selected among metallic mirrors or dielectric mirrors.

7. The device according to claim 4 wherein the said mirrors are structured in a solid transparent material having a refractive index as close as possible or matching that of the fluid immersing the particles to be trapped, in such a way that observation or light signal collection can be performed across the mirrors.

8. The device according to claim 4 wherein an additional layer of transparent material is placed between the reflective surface of the mirror and the focal plane of the mirror, in such a way that mirror's numerical aperture is increased with respect to a mirror that would operate in air.

9. The device according to claim 8 wherein the said layer of transparent material has a refractive index matching that of the material on the other side of the mirrors, in such a way that observation or light signal collection can be performed across the mirrors.

10. The device according to claim 1 wherein the said light source is a laser light source.

11. The device according to claim 1 wherein the wavelength of the said trapping light is selected in the near-infrared range.

12. A device according to claim 4 wherein the said light source is composed of one or an array of laser diodes, including vertical cavity surface emitting laser (VCSEL) diodes, each being spatially aligned with each of the focusing mirrors.

13. The device according to claim 4 further comprising a light detector and an imaging system to collect light signals from the optically trapped particles.

14. The device according to claim 13 wherein the focusing mirrors used for optical trapping are also part of the said imaging system.

15. The device according to claim 13 wherein the light detector is a light detector array coupled to the trap array trough an imaging system, in such a way that light signals from each trapped object is sent to the detector, and that the light signals collected from each trapped particle or from a portion of the trapped particle is collected onto a distinct area of the detector.

16. The device according to claim 13 wherein the said light detector is chosen among photomultipliers, charge coupled devices, complementary metal-oxide-semiconductors or photo-diode arrays.

17. The device according to claim 13 wherein the said light detector is a spectrometer.

18. The device according to claim 1 furthermore comprising one fluorescence excitation light source and produced light beam directed towards the trapping area to illuminate the trapped particles.

19. The device according to claim 18 wherein the said fluorescence light beam is focused onto the particles in the optical trap.

20. The device according to claim 1 furthermore comprising a fluidic system.

21. The device according to claim 20, wherein the fluidic system includes inlets, outlets and fluidic channels that allow a solution containing particles to be transported to-and away from-the trapping area.

22. The device according to claim 20 wherein the fluidic system has additional inlets and channels for transporting chemical reagents or molecules in solution to the objects in the optical traps.

23. The device according to claim 20 wherein the focusing mirrors, light sources, light detectors and fluidics are at least partially integrated in a unique miniaturized system.

24. The device according to claim 1 which is adapted to trap objects that are selected among bio-chemically functionalized dielectric or metallic particles, or biological cells, or cell fragments.

* * * * *